(12) United States Patent
Nelson et al.

(10) Patent No.: US 11,479,008 B2
(45) Date of Patent: Oct. 25, 2022

(54) APPARATUS AND METHOD FOR FOLDING

(71) Applicant: Curt G. Joa, Inc., Sheboygan Falls, WI (US)

(72) Inventors: Brian Nelson, Sheboygan Falls, WI (US); Thomas Muhs, Kiel, WI (US); Ryan Ferguson, Howards Grove, WI (US)

(73) Assignee: Curt G. Joa, Inc.

( * ) Notice: Subject to any disclaimer, the term of this patent is extended or adjusted under 35 U.S.C. 154(b) by 805 days.

(21) Appl. No.: 14/919,332

(22) Filed: Oct. 21, 2015

(65) Prior Publication Data

US 2016/0113821 A1    Apr. 28, 2016

Related U.S. Application Data

(60) Provisional application No. 62/068,353, filed on Oct. 24, 2014.

(51) Int. Cl.
| | |
|---|---|
| *B31F 1/00* | (2006.01) |
| *B31D 1/00* | (2017.01) |
| *A61F 13/15* | (2006.01) |

(52) U.S. Cl.
CPC .......... *B31D 1/00* (2013.01); *A61F 13/15747* (2013.01); *A61F 13/15764* (2013.01); *B31F 1/0016* (2013.01); *B31D 1/0081* (2013.01); *B31D 2201/00* (2013.01)

(58) Field of Classification Search
CPC ......... A61F 13/15747; A61F 13/15764; B31D 1/00; B31D 1/0081; B31D 2201/00; B31F 1/0016; B31F 1/0006; B31F 1/0045; B31B 50/58

USPC ........................................................ 493/425
See application file for complete search history.

(56) References Cited

U.S. PATENT DOCUMENTS

| | | | |
|---|---|---|---|
| 3,076,460 A | | 2/1963 | Harrison |
| 3,116,920 A | | 1/1964 | Geer et al. |
| 4,056,046 A | * | 11/1977 | Hughes .................. B31B 50/00 |
| | | | 493/12 |

(Continued)

OTHER PUBLICATIONS

Supplementary European Search Report pertaining to EP15853115, dated Mar. 2, 2018, 6 pages.

(Continued)

*Primary Examiner* — Sameh Tawfik
(74) *Attorney, Agent, or Firm* — Klintworth & Rozenblat IP LLP

(57) ABSTRACT

Discrete items are conveyed, preferably by a vacuum conveyor, in a machine direction toward a pair of rotating blades. A first intended target of folding, for instance a right portion of front and back panels of a diaper, travels up a ramp, raising the level of the intended target. A rotating blade passes under the intended target of folding, and folds the right portion of front and back panels of a diaper over. If desired, a second intended target of folding, for instance a left portion of front and back panels of a diaper, travels up a second ramp, raising the level of the intended target. A rotating blade passes under the second intended target of folding, and folds the left portion of front and back panels of a diaper over. The folded diaper then exits the folding system and travels downstream for further processing as desired.

20 Claims, 4 Drawing Sheets

(56) References Cited

U.S. PATENT DOCUMENTS

| | | | | |
|---|---|---|---|---|
| 4,307,800 | A | * | 12/1981 | Joa ................... A61F 13/15764 198/374 |
| 4,432,745 | A | * | 2/1984 | Eldridge ................ B31B 50/00 493/10 |
| 4,614,512 | A | * | 9/1986 | Capdeboscq .......... B65H 45/22 198/405 |
| 4,629,445 | A | * | 12/1986 | Toriyama ................ B31B 50/00 493/10 |
| 5,626,711 | A | * | 5/1997 | Herrmann ......... A61F 13/15577 156/163 |
| 6,837,840 | B2 | * | 1/2005 | Yonekawa ................ B42C 1/12 493/254 |
| 7,160,408 | B2 | * | 1/2007 | Otsubo ............. A61F 13/15699 156/161 |
| 7,399,266 | B2 | | 7/2008 | Aiolfi et al. |
| 8,357,256 | B2 | | 1/2013 | Dumas et al. |
| 8,439,814 | B2 | | 5/2013 | Piantoni et al. |
| 9,017,241 | B2 | * | 4/2015 | Lavon ............... A61F 13/15747 493/405 |
| 2002/0103468 | A1 | | 8/2002 | Nakakado et al. |
| 2003/0062121 | A1 | * | 4/2003 | Franklin ........... A61F 13/15747 156/285 |
| 2006/0218700 | A1 | * | 10/2006 | Uda ................. A61F 13/49001 2/400 |
| 2013/0130879 | A1 | * | 5/2013 | Schoon ............. A61F 13/15747 493/405 |
| 2013/0296152 | A1 | * | 11/2013 | Murakami ........ A61F 13/15747 493/405 |

OTHER PUBLICATIONS

European Patent Search Report for EP application No. 21198302.8 dated Feb. 17, 2022, 5 Pages.

* cited by examiner

APPARATUS AND METHOD FOR FOLDING

RELATED APPLICATION

This application claims the benefit of U.S. Provisional Patent Application Ser. No. 62/068,353, filed 24 Oct. 2014.

BACKGROUND OF THE INVENTION

The invention disclosed herein relates to apparatus and methods for folding pieces traveling on a production line. Although the description provided relates to diaper manufacturing, the apparatus and method are easily adaptable to other applications. Although the description provided relates to forming side panels of diapers, the apparatus and methods are easily adaptable to other products, other disposable products, other diaper types and other portions of diapers.

Generally, diapers comprise an absorbent insert or patch and a chassis, which, when the diaper is worn, supports the insert proximate a wearer's body. Additionally, diapers may include other various patches, such as tape tab patches, reusable fasteners and the like. The raw materials used in forming a representative insert are typically cellulose pulp, tissue paper, poly, nonwoven web, acquisition, and elastic, although application specific materials are sometimes utilized. Usually, most of the insert raw materials are provided in roll form, and unwound and applied in assembly line fashion.

In the creation of a diaper, multiple roll-fed web processes are typically utilized. To create an absorbent insert, the cellulose pulp is unwound from the provided raw material roll and pulverized by a pulp mill. Discrete pulp cores are formed by a core forming assembly and placed on a continuous tissue web. Optionally, super-absorbent powder may be added to the pulp core. The tissue web is wrapped around the pulp core. The wrapped core is debulked by proceeding through a calendar unit, which at least partially compresses the core, thereby increasing its density and structural integrity. After debulking, the tissue-wrapped core is passed through a segregation or knife unit, where individual wrapped cores are cut. The cut cores are conveyed, at the proper pitch, or spacing, to a boundary compression unit.

The diaper is built by sandwiching the formed core between a backsheet and a topsheet, and the combined web receives ears for securing the diaper about the waist of a baby.

Most products require some longitudinal folding. Folding of webs can be combined with elastic strands to make a cuff. Folding can be used to overwrap a stiff edge to soften the feel of the product. It can also be used to convert the final product into a smaller form to improve the packaging.

Diapers are typically formed in a machine direction in a generally flat condition. Formed diapers require folding both longitudinally to tuck the ears and associated tape or hook applicators into the diaper, and also cross-folded generally at a crotch region to stack the diapers prior to packaging. Larger portions of diapers, such as side portions of the front and rear panels of pant type diapers also require folding for compactness and packaging.

The folded product is then passed downstream to a packaging machine where the diapers are stacked and packaged and shipped for sale.

SUMMARY OF THE INVENTION

A system for folding is provided. At least one rotary blade is passed under an intended target of the folding, and the blade folds the intended target and passes the intended target downstream for further processing.

Importantly, the methods taught in the present application are applicable not only to diapers and the like, but in any web based operation. The folding techniques taught herein can be directed any discrete component of a manufactured article, i.e., the methods taught herein are not product specific. For instance, the present methods can be applied as easily with respect to diaper components as they can for feminine hygiene products.

Apparatus and methods are provided for folding discrete items such as diapers at high speeds. Discrete items are conveyed, preferably by a vacuum conveyor, in a machine direction toward a pair of rotating blades. The intended target of folding, for instance a right portion of front and back panels of a diaper, travels up a ramp, raising the level of the intended target. A rotating blade passes under the intended target of folding, and folds the right portion of front and back panels of a diaper over. If desired, another intended target of folding, for instance a left portion of front and back panels of a diaper, travels up a second ramp, raising the level of the intended target. A rotating blade passes under the intended target of folding, and folds the left portion of front and back panels of a diaper over. The folded diaper then exits the folding system and travels downstream for further processing as desired.

DESCRIPTION OF THE PREFERRED EMBODIMENT

Although the disclosure hereof is detailed and exact to enable those skilled in the art to practice the invention, the physical embodiments herein disclosed merely exemplify the invention which may be embodied in other specific structures. While the preferred embodiment has been described, the details may be changed without departing from the invention, which is defined by the claims.

It is noted that the present folding techniques and apparatus are described herein with respect to products such as diapers, but as previously mentioned, can be applied to a wide variety of processes in which components are required to be folded. The present methods can be used to fold a portion of a web, or discrete portions, as desired. The same apparatus and techniques can be used for ears, panels, hook materials, or any other situation in which folding is desired.

Importantly, the methods taught in the present application are applicable not only to diapers and the like, but in any web based operation. The folding techniques taught herein can be directed any component of a manufactured article desired to be folded, i.e., the methods taught herein are not product specific. For instance, the present methods can be applied as easily with respect to diaper components as they can for feminine hygiene products.

Figure 1:
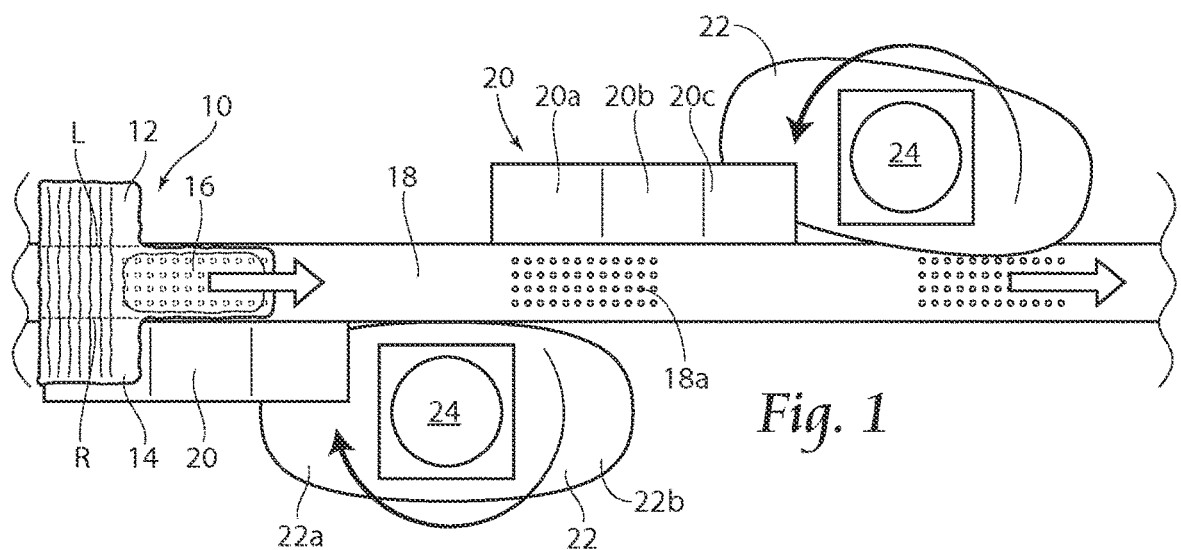
FIG. 1 is a top view of a representative web folding system, showing a single diaper product riding on a conveyor toward a pair of folding blades.

Referring now to FIG. 1, a top view of a representative web folding system is shown. A diaper product 10 riding on a conveyor 18, preferably a vacuum conveyor with vacuum commutation ports 18a, is conveyed toward a pair of folding blades 22.

Vacuum conveyor ports 18a can extend the entire length of vacuum conveyor 18, or extend for selected portions of conveyor 18, such as shown, or extend for an entire product length. In pant-type diapers, typically an absorbent core section 16 is contained in a midsection of diaper 10. Left side of panel 12 consists of both the front and rear left portions of panels of a previously formed diaper 10. Right side of panel 14 consists of both the front and rear left portions of panels of a previously formed diaper 10. Intended fold lines L for the left panel 12 and R for the right panel 14 are acted upon by the system.

The first intended target of the folding, fold line R for the right panel 14 is seen traveling onto ramp 20, the ramp 20 comprising three sections, a conveyor level 20a, a sloped midsection 20b, and a blade clearance level 20c. Two ramps 20 are provided, one for each of the intended fold lines L for the left panel 12 and R for the right panel 14.

Blade 22, with blade lobes 22a and 22b, is driven in the direction shown by rotor 24. Preferably, two independent, servo controlled blades 22 are programmed to aid in actively folding each part of the product 10.

Conveyor 18 travels in the machine direction at a first speed. The rotational speeds of blade 22 can match the conveyor speed (first speed), but in some instances, the rotational speeds of blade 22 are seen to have positive effects by having a rotational speed greater than or less than the conveyor speed.

Still referring to FIG. 1, the previous description describes a horizontal conveying surface 18 at a first elevation carrying at least a first portion 14 of an article 10 to be folded. The present invention is not limited to horizontal conveying surfaces 18, but also contemplates vertical or sloped conveying surfaces 18 (not shown). When the term elevation is used in the claims, the term is not to be limited to a vertical spacing relative to the conveying surface 18, but instead should be considered a spacing in any direction away, relative to conveying surface 18, e.g., for a vertical conveyor 18, the ramp 20 would actually elevate the first portion 14 of the article 10 in a horizontal direction relatively away from the vertical conveyor 18.

Figure 2:
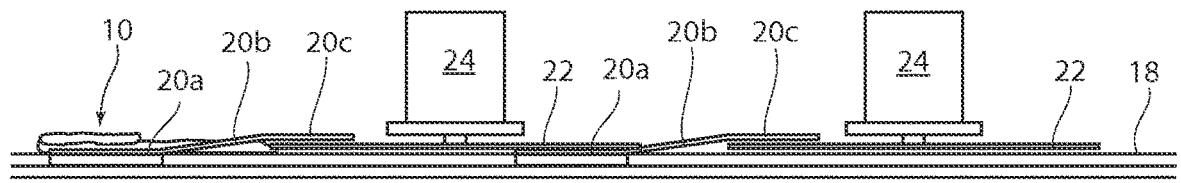
FIG. 2 is a side view of a folding system of the present invention.
Figure 3:
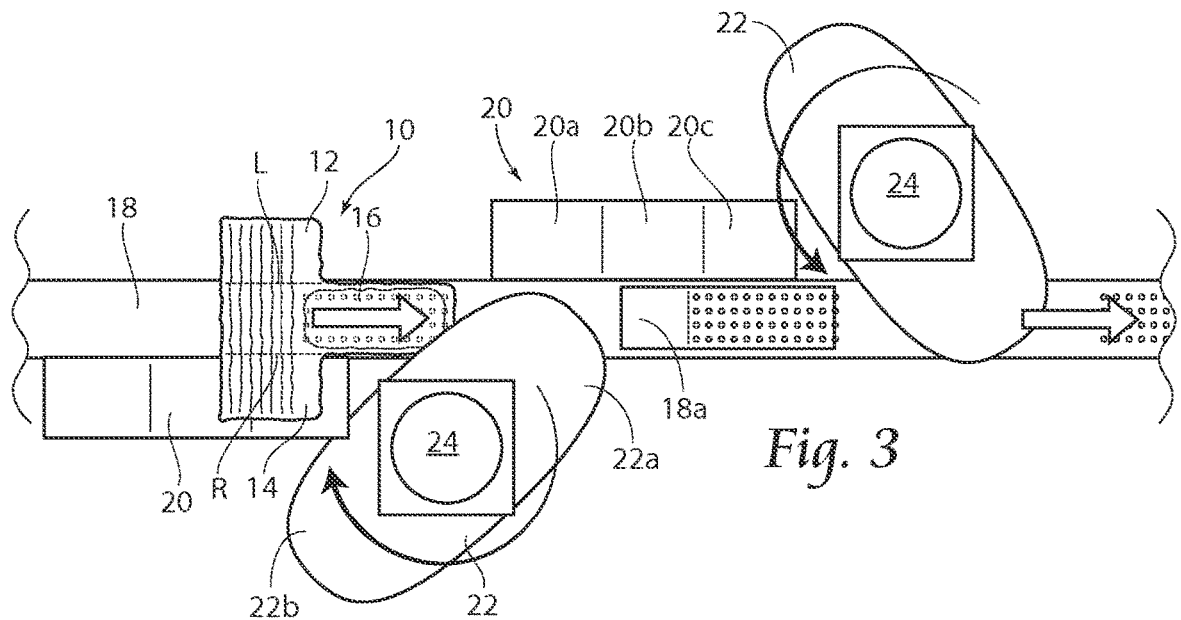
FIG. 3 is a top view of a representative web folding system, showing a single diaper product riding on a conveyor toward a pair of folding blades, with a right panel portion of the diaper riding up a ramp and approaching a rotating blade.
Figure 4:
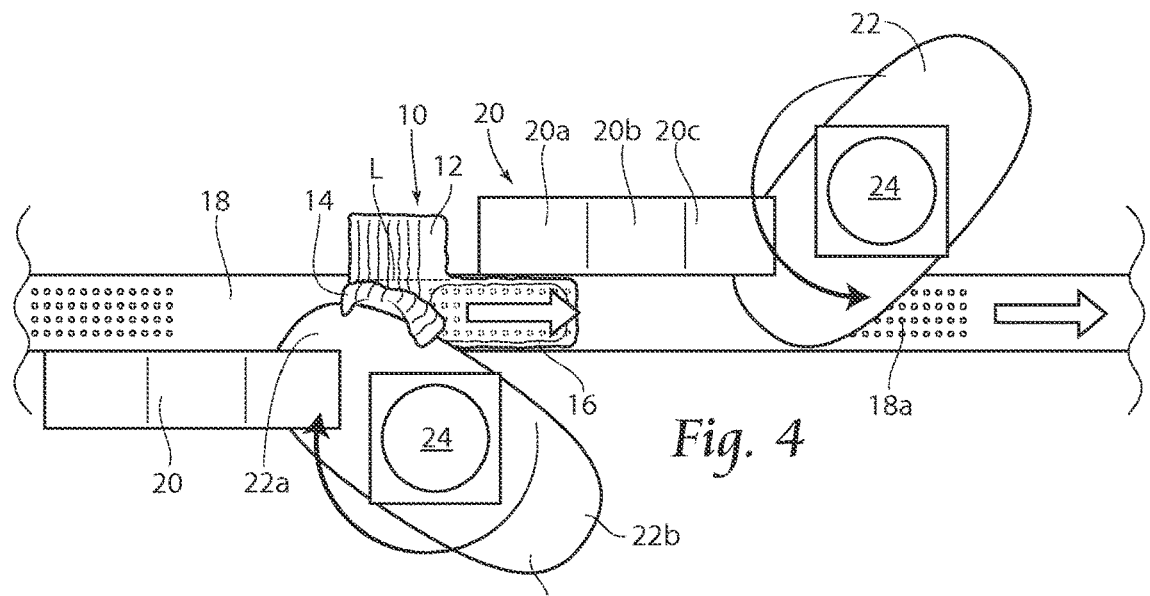
FIG. 4 is a top view of the right panel portion of the diaper being folded by a rotating blade.

Referring now to FIG. 2, a side view of a folding system of the present invention is shown. In this view, the ramp 20 comprising three sections, the conveyor level 20a, the sloped midsection 20b, and the blade clearance level 20c can be seen. Referring to the first ramp in the system (upstream), right panel 14 is shown entering onto the ramp 20 at the conveyor level 20a. As the right panel 14 travels downstream, the right panel 14 travels up ramp 20 via sloped midsection 20b, raising the level of the intended target, right panel 14. As the right panel travels onto blade clearance level 20c, as shown in FIG. 3, first rotating blade 22 passes under the intended target of folding, right panel 14, and passes under blade clearance level 20c. As lobe 22a of blade 22 rotates while the right panel 14 is carried by the blade clearance level 20c, blade 22 contacts the underside of right panel 14 and folds the right panel 14 of diaper 10 over along line R, as shown in FIG. 4.

Figure 5:
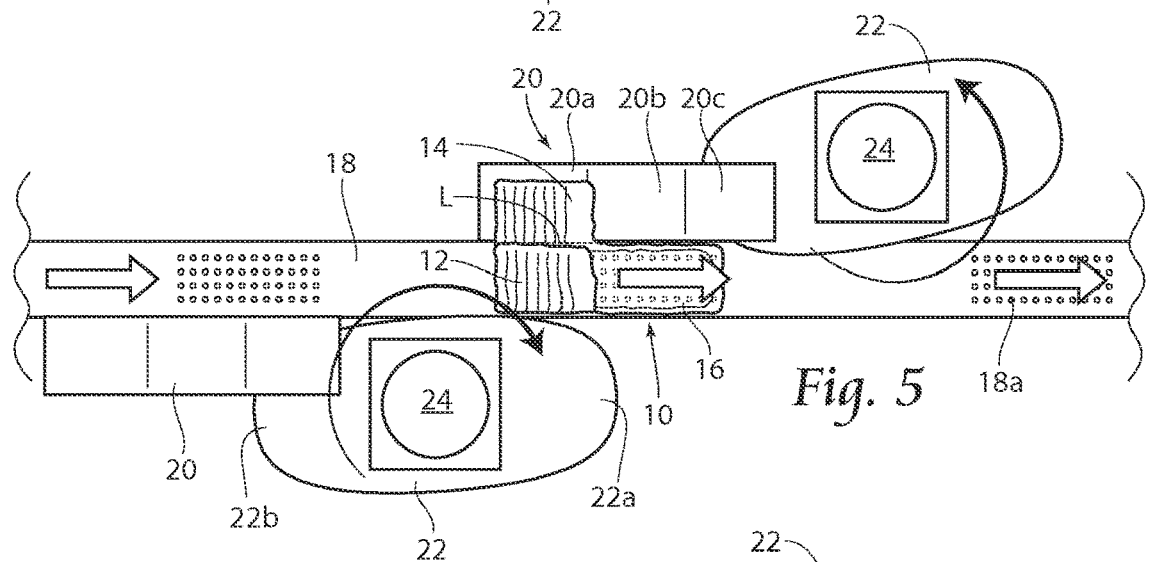
FIGS. 5 and 6 are top views of a representative web folding system, showing a folded over right panel portion, and showing a left panel portion of the diaper riding up a second ramp and approaching a second rotating blade.
Figure 6:
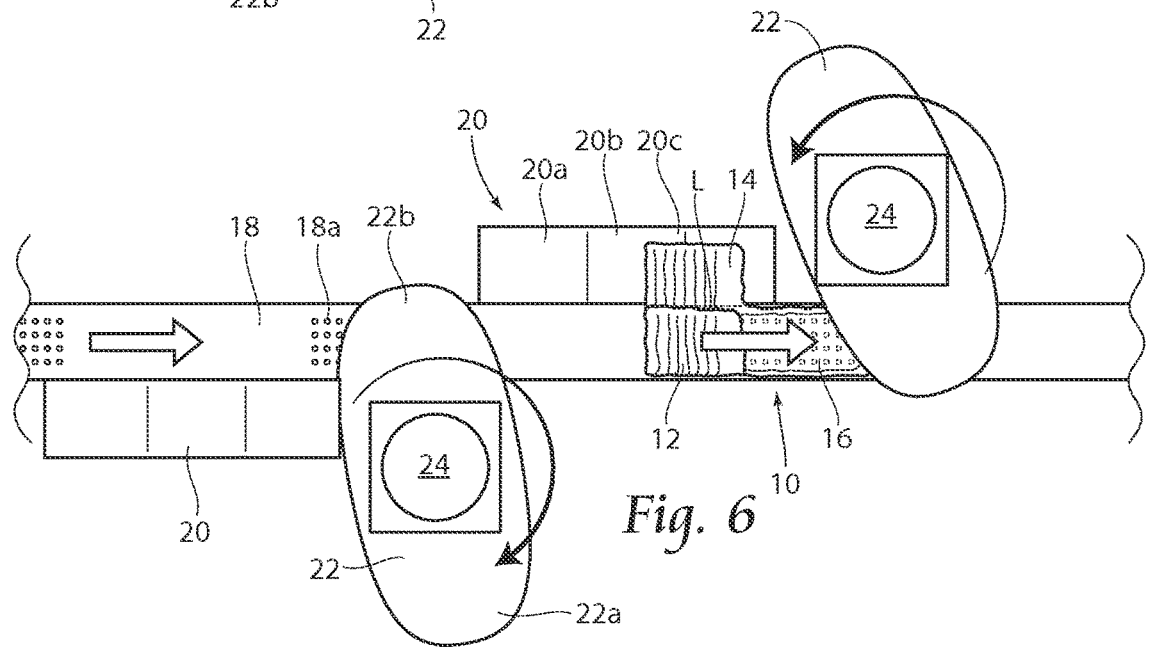
Figure 7:
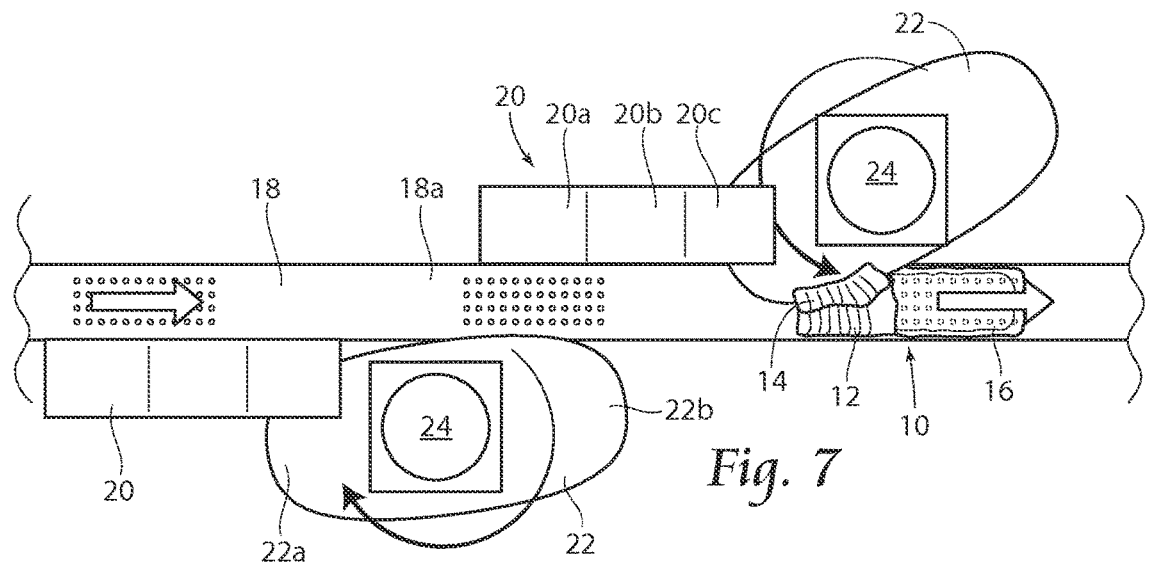
FIGS. 7 and 8 are top views of the left panel portion of the diaper being folded by a rotating blade.
Figure 8:
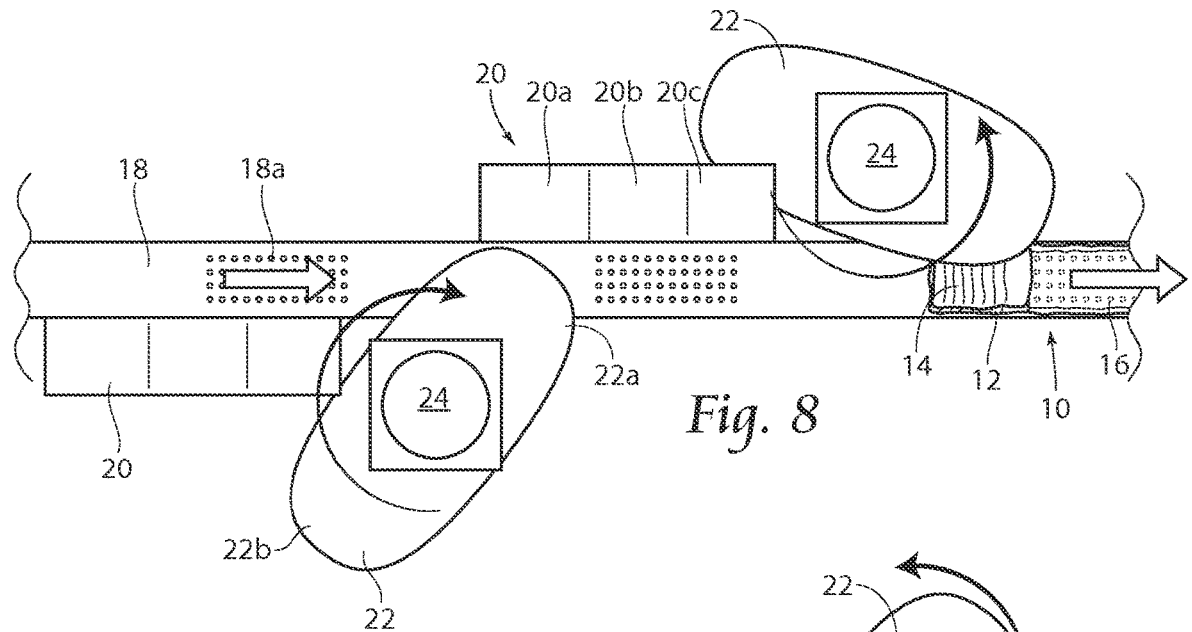
Figure 9:
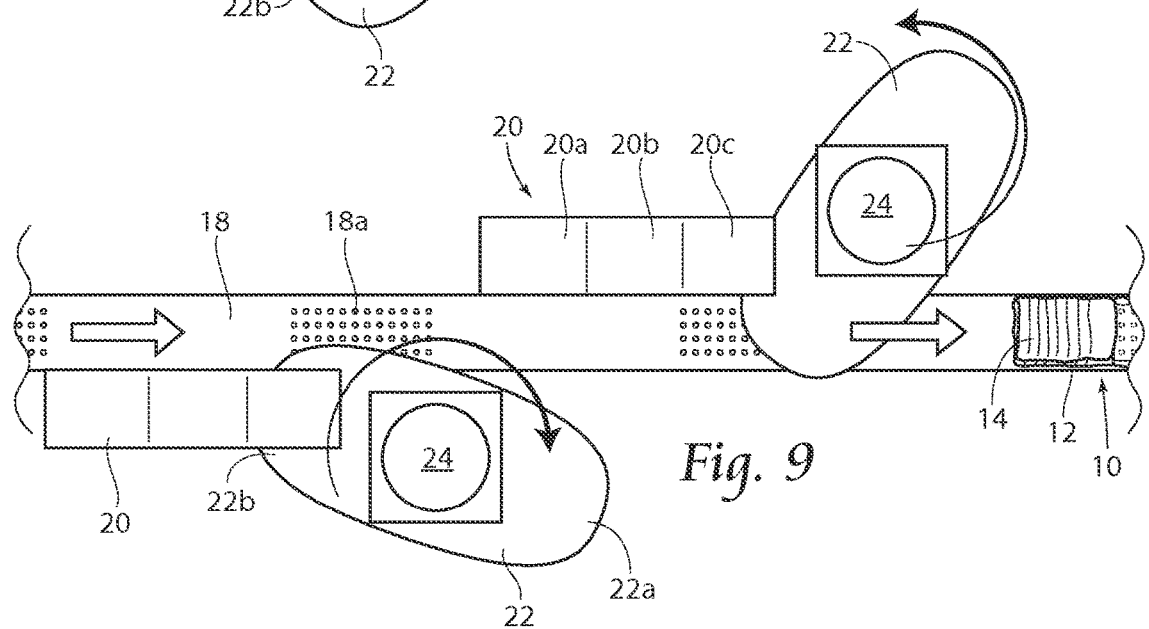
FIG. 9 is top view of the folded diaper exiting the folding system and being passed downstream for further processing.

Referring now to FIG. 5, with fold line R achieved, the half-folded diaper 10 is passed downstream. Left panel 12 enters onto the second ramp 20 at the conveyor level 20a. As the left panel 12 travels downstream, the right panel 14 travels up ramp 20 via sloped midsection 20b as shown in FIG. 6, raising the level of the intended target, left panel 12. As the left panel travels onto blade clearance level 20c, second rotating blade 22 passes under the intended target of folding, left panel 12, and passes under blade clearance level 20c. As lobe 22a of blade 22 rotates while the left panel 14 is carried by the blade clearance level 20c (FIG. 6), blade 22 contacts the underside of left panel 12 and folds the left panel 12 of diaper 10 over along line L, as shown in FIGS. 7 and 8. The diaper 10 is passed downstream as shown in FIG. 9, for further processing (e.g., folding or packaging) as desired.

Figure 10:
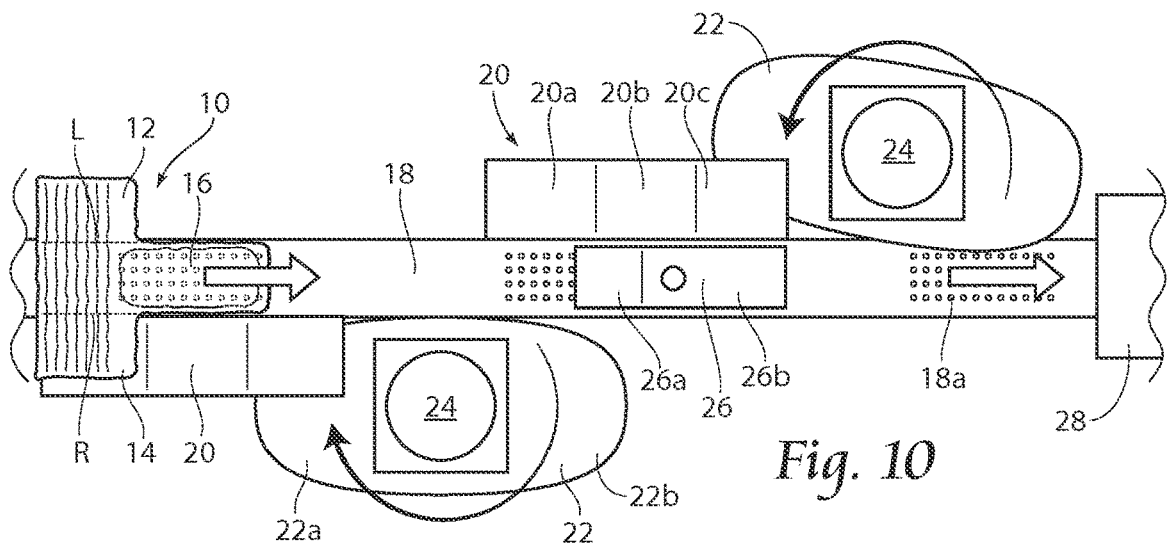
FIG. 10 is a top view of an alternate embodiment of the folding system shown in FIG. 1, the alternate embodiment including a tucker bar to maintain the first fold, and a tucker roller to maintain the first and second folds intact during downstream passage.
Figure 11:
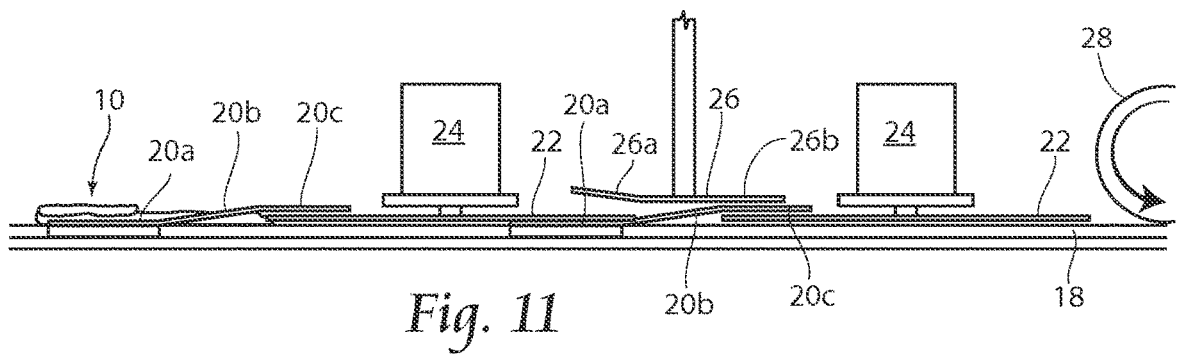
FIG. 11 is a side view of the folding system shown in FIG. 10.

Referring now to FIG. 10, a top view of an alternate embodiment of the folding system shown in FIG. 1 is shown. In this embodiment, a tucker bar 26 is provided at or above the blade clearance level 20c, as shown in cross section in FIG. 11. The tucker bar 26 maintains the first fold R in position while the diaper is passed downstream to the second rotating blade 22 to achieve the second fold as described previously. A tucker roller 28 is optionally provided to maintain the first and second folds R and L intact during downstream passage.

Figure 12A:
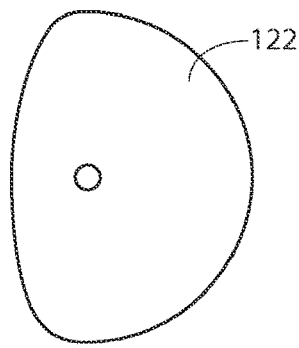
FIGS. 12a-c are top views of alternate blade configurations.
Figure 12B:
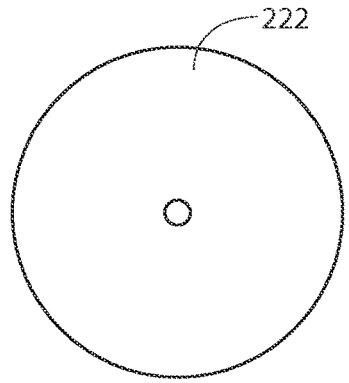
Figure 12C:
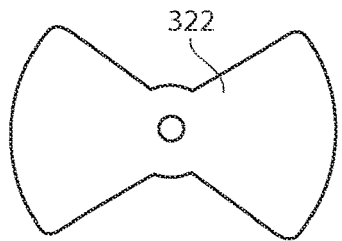

Referring to FIGS. 12a-c top views of alternate blade configurations are shown. In FIG. 12a, an oblong ear shaped blade 122 is shown. In FIG. 12b, a circular blade 222 is shown. In FIG. 12c, a bow-tie shaped blade 322 is shown. Blade shapes can be altered to improve folding performance. In addition, the web contacting surfaces of the blades 22, whether the web contacting surface be the top or the bottom of the blades 22, can be provided with varying coefficient-of-friction features. For instance, one portion of the blade, 22a could be provided with increased coefficient-of-friction features relative to a second portion of the blade, 22b. Alternatively, if as in FIG. 1, upstream and downstream blades 22 are used, the upstream blade 22 could provided with increased or decreased coefficient-of-friction features relative to the downstream blade 22.

The foregoing is considered as illustrative only of the principles of the invention. Furthermore, since numerous modifications and changes will readily occur to those skilled in the art, it is not desired to limit the invention to the exact construction and operation shown and described. While the preferred embodiment has been described, the details may be changed without departing from the invention, which is defined by the claims.

We claim:

1. An apparatus for folding a product, the apparatus comprising:

a conveying surface configured to carry, along a machine direction, at least a midsection of an article to be folded;

a carrying surface configured to carry a first panel of said article;

a first blade configured to pass between said conveying surface and said carrying surface and configured to create a first fold in said article via folding over at least a portion of said first panel along a first fold line onto said midsection; and wherein said first fold line is parallel with said machine direction.

2. The apparatus of claim 1 further comprising:

a second carrying surface configured to carry at least a second panel of said article;

a second blade configured to create a second fold in said article via folding over at least a portion of said second panel along a second fold line onto at least one of said midsection and first panel.

3. The apparatus of claim 2 wherein said second blade comprises a rotating blade configured to rotate independently from said conveying surface and configured to rotate into contact with said at least a portion of said second panel.

4. The apparatus of claim 2 wherein said second blade is configured to fold over said at least a portion of said second panel onto said first panel.

5. The apparatus of claim 2 wherein said second blade comprises a first zone having a first coefficient of friction and a second zone having a second coefficient of friction different than said first coefficient of friction.

6. The apparatus of claim 2 wherein said first and second blades have different coefficients of friction.

7. The apparatus of claim 2 wherein said second carrying surface comprises a first portion, a midsection portion, and a blade clearance portion;

wherein said midsection portion of said second carrying surface couples said first portion of said second carrying surface with said blade clearance portion of said second carrying surface;

wherein said second blade is configured to pass over said first panel of said article and said midsection of said article; and wherein said second blade is configured to pass under said second panel of said article and said blade clearance portion of said second carrying surface to create said second fold.

8. The apparatus of claim 1 wherein said first blade comprises a rotating blade configured to rotate independently from said conveying surface and configured to rotate into contact with said first panel.

9. The apparatus of claim 1 wherein said first blade comprises a first zone having a first coefficient of friction and a second zone having a second coefficient of friction different than said first coefficient of friction.

10. The apparatus of claim 1 wherein said carrying surface comprises a first portion, a midsection portion, and a blade clearance portion;

wherein said midsection portion of said carrying surface couples said first portion of said carrying surface with said blade clearance portion of said carrying surface;

wherein said first blade is configured to pass over said midsection of said article; and wherein said first blade is configured to pass under said first panel of said article and said blade clearance portion of said carrying surface to create said first fold.

11. The apparatus of claim 1, wherein a ramp comprising said carrying surface is configured to raise a level of said first panel with respect to said conveying surface as said midsection is carried by said conveying surface along said machine direction.

12. The apparatus of claim 11, wherein said conveying surface moves independently from said carrying surface.

13. The apparatus of claim 1 further comprising a tucker bar positioned above said conveying surface and downstream of said carrying surface, said tucker bar configured to maintain said first fold as said article is carried thereby.

14. The apparatus of claim 1, wherein a shape of said first blade comprises one of an oblong ear shape, a circular shape, and a bow-tie shape.

15. A method of folding a product, the method comprising:

carrying at least a midsection of an article to be folded on a conveying surface along a machine direction;

carrying a first panel of the article on a first carrying surface; and creating a first fold in the article by passing a first blade between the conveying surface and the first carrying surface in order to fold over at least a portion of the first panel of the article onto the midsection of the article along a first fold line that is parallel with the machine direction.

16. The method of claim 15 wherein creating the first fold comprises rotating the first blade independently from the conveying surface and into contact with the first panel of the article.

17. The method of claim 16 wherein creating the second fold comprises rotating the second blade independently from the conveying surface and into contact with the second panel of the article.

18. The method of claim 15 further comprising:

carrying at least a second panel of the article on a second carrying surface; and creating a second fold in the article with a second blade that folds over at least a portion of the second panel of the article onto the midsection of the article, the first panel of the article, or a combination thereof.

19. The method of claim 15 wherein carrying the first panel of the article comprises elevating the first panel in a direction away from the conveying surface with a ramp while the conveying surface carries the midsection of the article along the machine direction.

20. The method of claim 15 further comprising providing the carrying surface with a first level, a blade clearance level, and a midsection level coupling the first level to the blade clearance level;

wherein the first blade passes under the blade clearance level when creating the first fold.

* * * * *